(12) United States Patent
Suzuki (10) Patent No.: US 9,072,467 B2
(45) Date of Patent: Jul. 7, 2015

(54) OPHTHALMOLOGIC PHOTOGRAPHY APPARATUS

(75) Inventor: Takayoshi Suzuki, Hamamatsu (JP)

(73) Assignee: KOWA COMPANY LTD. (JP)

( * ) Notice: Subject to any disclaimer, the term of this patent is extended or adjusted under 35 U.S.C. 154(b) by 720 days.

(21) Appl. No.: 13/138,215

(22) PCT Filed: Aug. 26, 2009

(86) PCT No.: PCT/JP2009/064823
§ 371 (c)(1),
(2), (4) Date: Jul. 20, 2011

(87) PCT Pub. No.: WO2010/087046
PCT Pub. Date: Aug. 5, 2010

(65) Prior Publication Data
US 2011/0273538 A1    Nov. 10, 2011

(30) Foreign Application Priority Data

Jan. 30, 2009 (JP) .................................. 2009-019888

(51) Int. Cl.
| | |
|---|---|
| *H04N 13/02* | (2006.01) |
| *A61B 3/12* | (2006.01) |
| *A61B 3/13* | (2006.01) |
| *A61B 3/14* | (2006.01) |

(52) U.S. Cl.
CPC . *A61B 3/12* (2013.01); *A61B 3/132* (2013.01); *G06T 2207/30041* (2013.01); *G06T 2207/10012* (2013.01); *A61B 3/14* (2013.01)

(58) Field of Classification Search
USPC .............................. 348/49; 351/206; 382/154
See application file for complete search history.

(56) References Cited

U.S. PATENT DOCUMENTS

| 7,290,880 | B1 | 11/2007 | Yaron et al. .................. 351/206 |
| 2007/0132951 | A1* | 6/2007 | Suzuki ........................ 351/206 |
| 2009/0180178 | A1* | 7/2009 | Luecke et al. ............... 359/376 |

FOREIGN PATENT DOCUMENTS

| JP | 2977607 | 7/1992 |
| JP | 07124118 | 5/1995 |
| JP | 7124118 | 5/1995 |
| JP | 3542167 | 12/1995 |
| JP | 2006 75449 | 3/2006 |
| JP | 2006075449 | 3/2006 |
| JP | 2006 87793 | 4/2006 |
| JP | 2006087793 | 4/2006 |
| JP | 2006314650 | 11/2006 |
| JP | 2008 18043 | 1/2008 |
| JP | 2008029634 | 3/2008 |
| WO | 2008029634 | 3/2008 |

* cited by examiner

*Primary Examiner* — Thai Tran
*Assistant Examiner* — Stephen Smith
(74) *Attorney, Agent, or Firm* — Adams & Wilks (57) ABSTRACT

A light beam reflected from an ocular fundus is split into a pair of right and left light beams by a two-aperture stop disposed in a position conjugate with an anterior ocular segment of an eye to be examined. The pair of right and left ocular fundus images having a parallax is formed as intermediate images from the split light beams at the position of a photographic mask. The optical path of the pair of ocular fundus images formed as intermediate images is split by a pair of optical path splitting lenses disposed in a position substantially conjugate with the two-aperture stop. One ocular fundus image is re-formed on half of an imaging plane of an imaging element, and the other ocular fundus image is reformed separately on the other half of the imaging plane. With such a structure, two ocular fundus images for three dimensional viewing can be efficiently obtained without using a prism for splitting the optical path.

11 Claims, 9 Drawing Sheets

OPHTHALMOLOGIC PHOTOGRAPHY APPARATUS

CROSS-REFERENCE TO RELATED APPLICATIONS

This application is a U.S. national stage application of International Application No. PCT/JP2009/064823 filed Aug. 26, 2009, claiming a priority date of Jan. 30, 2009, and published in a non-English language.

TECHNICAL FIELD

The present invention relates to an ophthalmologic photography apparatus, and more specifically to an ophthalmologic photography apparatus such as a fundus camera capable of observing and photographing a pair of ocular fundus images having a parallax for three-dimensional viewing.

BACKGROUND ART

Conventionally, fundus cameras are known in which light that is incident on an ocular fundus via an objective lens and reflected therefrom is split to provide split light beams which are formed into images by a pair of image-forming optical systems to observe and photograph a pair of right and left ocular fundus images for three-dimensional viewing (Patent Documents Nos. 1 and 2).

There are also ophthalmologic photography apparatuses in which an ocular fundus to be examined are imaged by splitting the optical path using a two-aperture stop to provide two split ocular fundus images which are observed for focus adjustment (Patent Document 3).

PRIOR ART DOCUMENTS

Patent Document 1: Japanese Patent No. 3542167
Patent Document 2: Japanese Patent No. 2977607
Patent Document 3: Japanese Laid-Open Patent Publication No. 2008-18043

SUMMARY OF INVENTION

Problems to be Solved

The ophthalmologic photography apparatuses proposed in Patent Documents Nos. 1 and 2 have disadvantages in that each of the right and left images having a parallax must be formed independently, and the right and left optical paths must be transposed using an optical path splitting prism in order to observe the images with both eyes or to photograph the images using an imaging element.

In order to photograph the two right and left images into proximity with each other using one imaging element, the interval between the right and left optical paths must be determined in accordance with the imaging element. This necessitates prisms at many locations, and therefore the apparatus is large by necessity, preventing the realization of a compact and inexpensive ophthalmologic photography apparatus.

In Patent Document 3, focusing is performed by observing the two ocular fundus images split into the right and left via the two-aperture stop, but no structure is proposed wherein the two formed ocular fundus images are re-formed by splitting the optical path again to obtain a pair of images having a parallax for three-dimensional viewing.

The present invention was made by taking the above-mentioned facts into consideration, and an object thereof is to provide an ophthalmologic photography apparatus that allows a pair of ocular fundus images having a parallax for three-dimensional viewing to be observed and photographed with a simple construction.

Means for Solving the Problems

The present invention is an ophthalmologic photography apparatus wherein an image of an ocular fundus of an eye to be examined is photographed by electronic imaging means, comprising:

a two-aperture stop disposed in a position conjugate with an anterior ocular segment of the eye to be examined for splitting a light beam reflected from the ocular fundus of the eye to be examined into a pair of right and left light beams having a parallax;

a first image-forming optical system that forms from the split light beams a pair of right and left optical fundus images as intermediate images; and a second image-forming optical system that separates the pair of ocular fundus images formed as intermediate images into the right and left and re-forms them on an imaging plane of the electronic imaging means.

The second image-forming optical system is comprised of a pair of optical path splitting lenses that is disposed in a position substantially conjugate with the two-aperture stop to split an optical path from the pair of ocular fundus images formed as intermediate images and separately re-forms the pair of ocular fundus images on the imaging plane of the electronic imaging means. A relay lens having a focal plane at a plane on which the intermediate images are formed is disposed between the pair of optical path splitting lenses and the plane on which the intermediate images are formed. In the second image-forming optical system, the distance between the lens center axes of the pair of optical path splitting lenses is set to be equal to substantially half of the entire length of the imaging plane along a direction orthogonal to the center axes.

Effect of the Invention

In the present invention, a pair of right and left ocular fundus images having a parallax formed as temporary intermediate images is separated into the right and left by optical path splitting lenses and re-formed on the imaging plane of the imaging means. This advantageously allows two ocular fundus images for three-dimensional viewing to be produced without using an optical path splitting prism, thus providing a compact, simply structured stereoscopic ophthalmologic photography apparatus.

MODE OF CARRYING OUT THE INVENTION

The present invention will be described in detail hereinafter with reference to the embodiments shown in the drawings. A fundus camera will be used as an example of an ophthalmologic photography apparatus in the following description of the embodiments.

Embodiments

Figure 1:
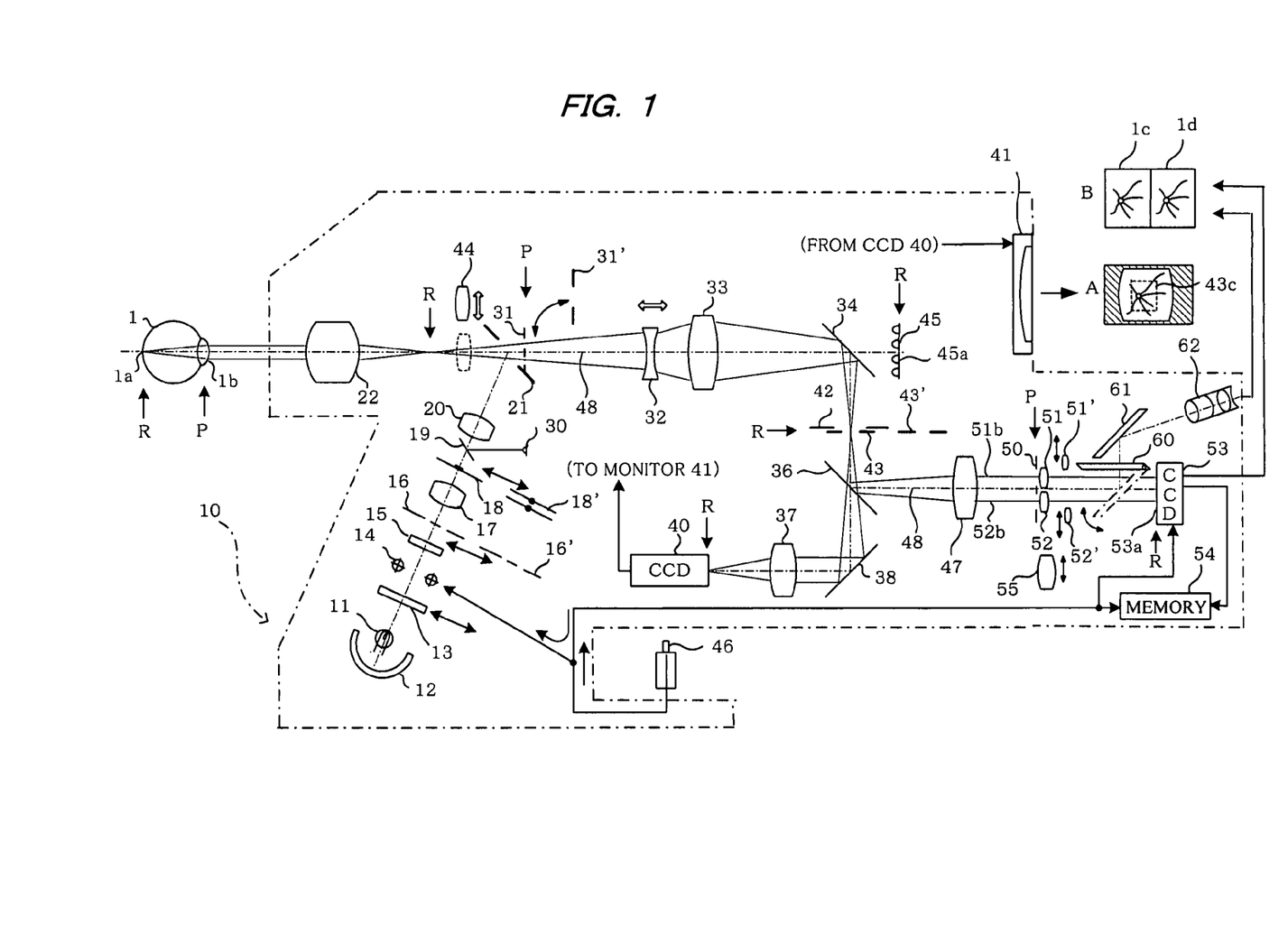
FIG. 1 is an optical diagram showing the entire structure of an ophthalmologic photography apparatus.

FIG. 1 shows a fundus camera 10 capable of stereoscopic photography (three-dimensional photography) and monocular photography. The illustration in FIG. 1 is primarily that of stereoscopic photography, and a switch to each corresponding optical element can be made when monocular photography is performed.

The fundus camera 10 is provided with an illumination optical system for illuminating the ocular fundus, and an optical system for forming an image of the illuminated ocular fundus. In the illumination optical system, light emitted from a light source 11 such as a halogen lamp and light reflected by a concave mirror 12 are converted into infrared light via a visible-blocking/infrared-transmitting filter 13 that can be inserted into and withdrawn from the optical path. The infrared light is transmitted through a strobe 14 and diffused by a diffusion plate 15 to illuminate a ring slit 16 for stereoscopic photography that is disposed in a position conjugate with an anterior ocular segment (pupil) 1b of an eye 1 to be examined. A switch from the ring slit 16 to a monocular ring slit 16' can be made when monocular photography is performed.

Illuminating light through the ring slit 16 passes through a lens 17 and a black spot plate 18 for removing the reflection from an objective lens 22, as well as through a half mirror 19 and a relay lens 20, and is reflected by an apertured total-reflection mirror 21 provided with an aperture in the center.

Figure 9A:
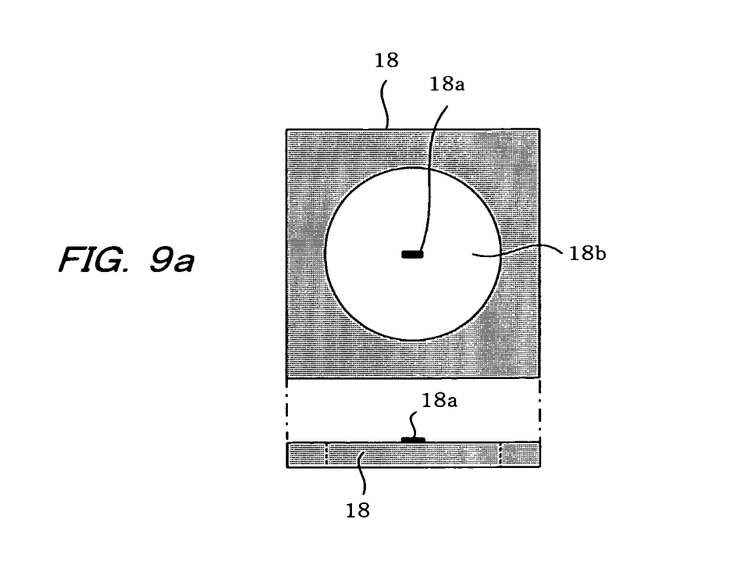
FIG. 9a is an illustrative view showing the structure of a black spot plate during stereoscopic photography.
Figure 9B:
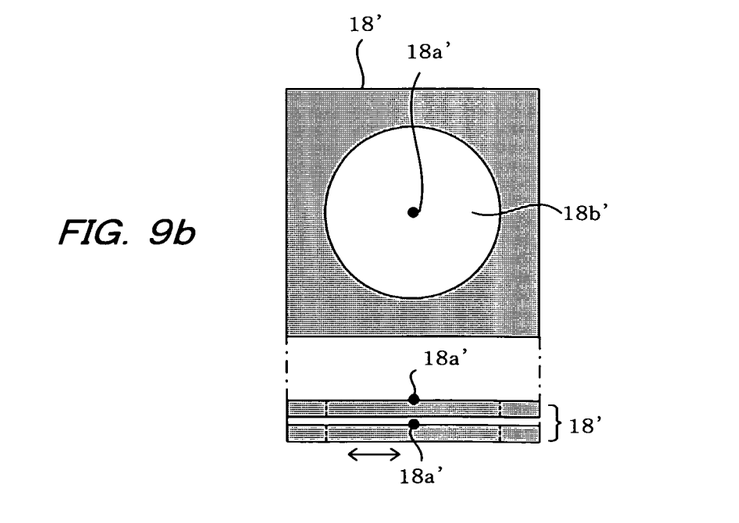
FIG. 9b is an illustrative view showing the structure of a black spot plate during monocular photography.

The black spot plate 18 is constructed as a flat plate in which a black spot 18a has been vapor-deposited on the center of a transparent glass plate 18b, as shown in FIG. 9a. The black spot plate 18 is used for stereoscopic photography, and, as shown in FIG. 9b, a switch can be made to a black spot plate 18' when monocular photography is performed. The black spot plate 18' is constructed as two close flat plates in which a black spot 18a' has been vapor-deposited on the center of a transparent glass plate 18b'. The two plates of the black spot plate 18' can be moved relative to each other in a direction orthogonal to the axis of illuminating light to adjust the position of the two black spots 18a'.

The illuminating light reflected by the apertured total-reflection mirror 21 is incident through the objective lens 22 on the ocular fundus 1a from the anterior ocular segment 1b of the eye 1 to be examined to illuminate the ocular fundus 1a with infrared light.

Figure 3A:
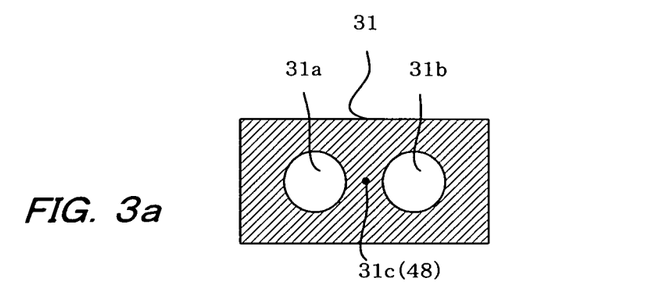
FIG. 3a is a front view of a two-aperture stop.
Figure 3B:
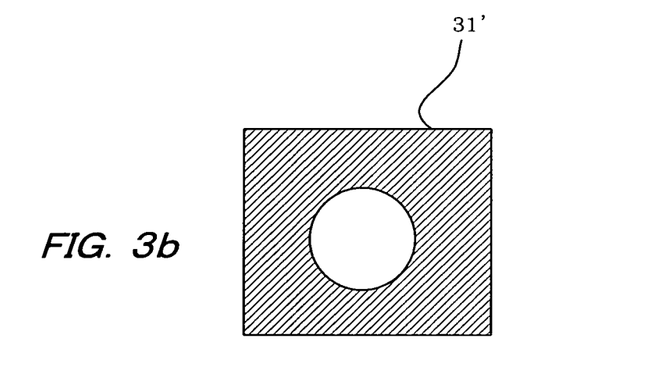
FIG. 3b is a front view of a single-aperture stop.

The light reflected from the ocular fundus 1a is received via the objective lens 22, is transmitted through the aperture in the apertured total-reflection mirror 21, and is incident on a two-aperture stop 31 used as a photographic stop and provided with two circular apertures 31a, 31b such as those shown in FIG. 3a. The two-aperture stop 31 is disposed in a position that is substantially conjugate with the anterior ocular segment 1b of the eye 1 to be examined in an arrangement in which the center 31c of the stop is in alignment with the photographic optical axis 48. The optical path of the light reflected from the ocular fundus is split in a right-left arrangement by the two apertures 31a, 31b of the two-aperture stop 31. The pair of right and left light beams from the ocular fundus 1a with the split optical path is incident on a focusing lens 32, which can move along the photographic optical axis to correct the positional deviation of the ocular fundus image-forming position caused by the individual differences in the diopter of the eye to be examined. A single-aperture stop 31' as shown in FIG. 3b can be inserted into the optical path instead of the two-aperture stop 31 in a position conjugate with the anterior ocular segment when monocular photography is performed.

The ocular fundus images passing through the focusing lens 32 are then transmitted through an image-forming lens 33, reflected by a half mirror 34, and made incident on an infrared-transmitting/visible-reflecting mirror (optical path splitting means) 36 via photographic masks 42, 43 disposed in a position conjugate with the ocular fundus 1a and used to determine a photographic range for the ocular fundus. The focusing lens 32 and the image-forming lens 33 constitute a first image-forming optical system that forms the pair of right and left ocular fundus images having a parallax via the two-aperture stop 31 as intermediate images at the position of the photographic mask 43.

Figure 4A:
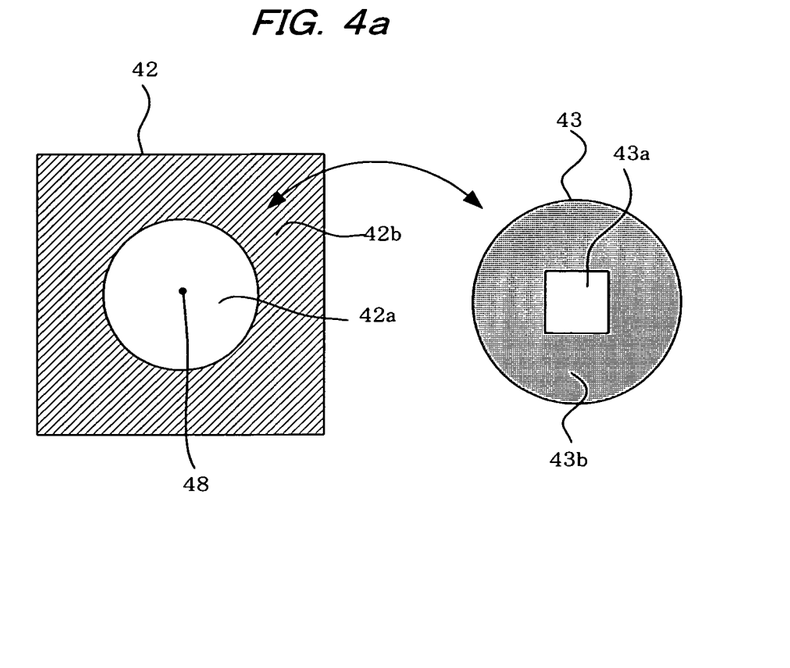
FIG. 4a is a front view of photographic masks for stereoscopic photography and monocular photography shown separately.
Figure 4B:
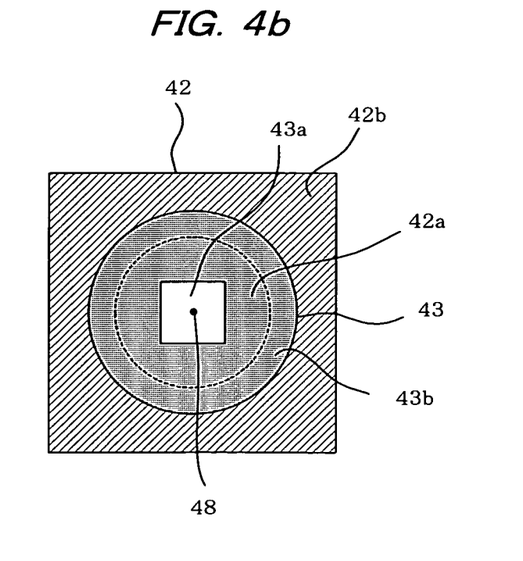
FIG. 4b is a front view of photographic masks for stereoscopic photography and monocular photography in an overlapping arrangement.

As shown in FIG. 4a, the photographic mask 42 is a photographic mask for monocular photography composed of a circular opening part 42a and a light-shielding part 42b impermeable to all wavelengths. The photographic mask 43 is a photographic mask for stereoscopic photography, and is constructed of a rectangular opening part 43a and a region 43b that has a circular periphery and transmits only infrared light. The photographic mask 42 is fixedly disposed in the optical path in a manner in which the center of the mask coincides with the photographic optical axis 48, and the photographic mask 43 is, as shown in FIG. 4b, inserted into the optical path so that the center of the mask is in line with the photographic optical axis 48 when stereoscopic photography is performed. The photographic mask 43 is, as shown in FIG. 4a, withdrawn from the optical path to make the photographic mask 42 effective when monocular photography is performed.

Referring again to FIG. 1, the infrared light transmitted through the infrared-transmitting/visible-reflecting mirror 36 is reflected by a mirror 38, passes through a lens 37, and is made incident on an imaging element (imaging means) 40 constructed of a CCD or the like sensitive to infrared light to produce a signal that is input to a monitor 41.

A relay lens 47 is disposed in order to form the images of the exit pupil in the first image-forming optical system on a second image-forming optical system (described below). Visible light reflected by the mirror 36 is incident through the relay lens 47 on a two-aperture stop 50 disposed in a position conjugate with the anterior ocular segment 1b. The two-aperture stop 50 is a stop similar to the two-aperture stop 31 shown in FIG. 3a, and a pair of optical path splitting lenses 51, 52 is disposed adjacent to the two-aperture stop 50 (that is, in a position substantially conjugate with the two-aperture stop 31). As described below, the pair of optical path splitting lenses constitutes the second image-forming optical system that splits the optical path from the photographic mask 43 so that the pair of right and left ocular fundus images formed as intermediate images at the position of the photographic mask 43 is re-formed separately into the right and left without overlapping with each other. In this arrangement, the optical path splitting lenses 51, 52 are preferably disposed at equal intervals in relation to the photographic optical axis 48, that is, in axial symmetry in relation to the photographic optical axis 48.

An imaging element (imaging means) 53 constructed of a CCD or the like sensitive to visible light has an imaging plane 53a disposed on an image-forming plane of the second image-forming optical system. A return mirror 60 is disposed between the optical path splitting lenses 51, 52 and the imaging element 53. The separated pair of right and left ocular fundus images can be observed with the naked eye using an eyepiece (binocular viewing means) 62 via a mirror 61 in cases in which the visible-blocking/infrared-transmitting filter 13 is withdrawn from the optical path and the return mirror 60 is inserted into the optical path.

The ocular fundus images taken by the imaging element 53 can be stored in a memory 54 and loaded into an external computer (not shown), displayed on a monitor 41, or output to a printer (not shown).

A switch can be made from the pair of optical path splitting lenses 51, 52 having the same magnification to another pair of optical path splitting lenses 51', 52' having different magnifications, and a pair of ocular fundus images can be photographed at the different magnifications. When a switch is made to the pair of optical path splitting lenses 51', 52' having different magnifications, a switch is made accordingly from the photographic mask 43 for stereoscopic photography to a photographic mask 43' having a different opening window.

When monocular photography is performed, an image-forming lens 55 for monocular photography is inserted into the optical path instead of the optical path splitting lenses 51, 52, and the two-aperture stop 50 is withdrawn from the optical path.

A focus-dot light source 30 is provided in the illumination optical system, and a light beam from the light source 30 is made incident on the ocular fundus 1a via the half mirror 19. The examiner can observe the focus dot and bring the ocular fundus into focus because the position of the focus dot varies in accordance with the movement of the focusing lens 32.

In the initial alignment step, the insertion of the anterior ocular segment lens 44 allows the examiner to confirm the image of the anterior ocular segment 1b of the eye 1 to be examined on the monitor 41. Any of the LED light sources of internal fixed lamps 45 formed of a plurality of LED light sources 45a is switched on during alignment and focusing, and the examiner can accurately perform alignment and focusing by having the subject concentrate on the fixed lamp.

Figure 2:
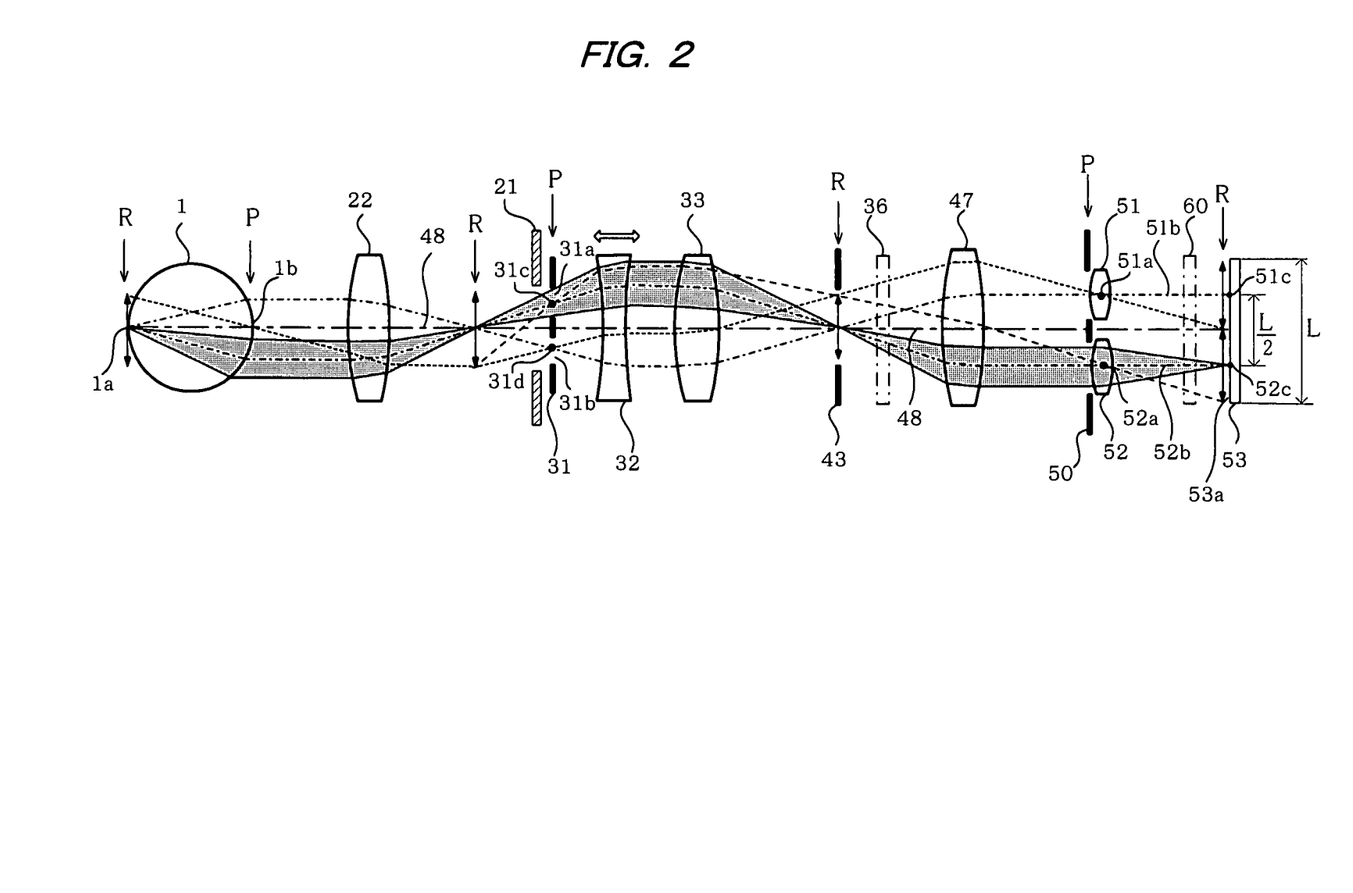
FIG. 2 is an optical diagram showing the principal optical structure employed when a stereoscopic photography is performed using the optical arrangement shown in FIG. 1.

FIG. 2 shows the principal part of the optical system for forming an image of an ocular fundus when stereoscopic photography is performed. The same symbols are applied to elements that are the same as in FIG. 1.

The position conjugate with the ocular fundus 1a of the eye 1 to be examined is shown as R in FIGS. 1 and 2, and the position conjugate with the anterior ocular segment (specifically, the pupil) is shown as P.

The two-aperture stops 31, 50 and the optical path splitting lenses 51, 52 in FIGS. 1 and 2 are illustrated so that the optical path is split into top and bottom parts in the drawings, but the path is actually split in a right-left arrangement (in the direction perpendicular to the plane of the paper). However, it is difficult to illustrate a state in which the light beams are split in a right-left arrangement on the plane of the drawing. Therefore, the two-aperture stops 31, 50 and the optical path splitting lenses 51, 52 in FIGS. 1 and 2 are illustrated as when seen from a direction orthogonal to the plane of the paper as a matter of convenience.

In the fundus camera thus constructed, the visible-blocking/infrared-transmitting filter 13 is inserted into the illumination optical path, and the ocular fundus is therefore illuminated by infrared light when the halogen lamp 11 is switched on.

When monocular photography is performed, the ring slit 16', single-aperture stop 31', and the image-forming lens 55 for monocular photography are inserted into the optical path, and the photographic mask 43, two-aperture stop 50, and the like are withdrawn from the optical path.

The ocular fundus image illuminated by infrared light is formed at the position of the photographic mask 42 by the objective lens 22, focusing lens 32, and image-forming lens 33, transmitted through the infrared-transmitting/visible-reflecting mirror 36, and re-formed as a moving image on the imaging plane of the imaging element 40 by the image-forming lens 37. The ocular fundus image can therefore be displayed as a black-and-white image on the monitor 41, and observed in a non-mydriatic mode by the examiner via the monitor 41. At this time, the magnification of the image formed on the imaging element 40 is made less than the magnification of the image formed by the second image-forming optical system. This allows a wide-angle ocular fundus image to be observed, making an alignment easy in the non-mydriatic mode. The ocular fundus of the eye to be examined can also be brought into focus by observing the focus dot produced by the light source 30.

Since the anterior ocular segment lens 44 is inserted in the initial steps of alignment, the examiner observes an image of the anterior ocular segment 1b of the eye 1 to be examined on the monitor 41 to perform alignment.

After alignment is complete, a shutter switch 46 is operated to produce a signal, which is input to the imaging element 53 and the memory 54. This activates the imaging element 53 in preparation for taking a still image of the ocular fundus. In synchronization with the operating signal of the shutter switch 46, a signal for emitting light is transmitted from the imaging element 53 to the strobe 14, which then emits light. The ocular fundus illuminated by the light emitted from the strobe 14 is photographed as a still image by the imaging element 53.

When stereoscopic photography is performed, the ring slit 16, two-aperture stop 31, and optical path splitting lenses 51, 52 are inserted into the optical path instead of the ring slit 16', single-aperture stop 31', and image-forming lens 55. The two-aperture stop 50 and photographic mask 43 are also inserted into the optical path.

The optical path of the light beam from the ocular fundus 1a is split into right and left parts by the two-aperture stop 31. The focusing lens 32 and the image-forming lens 33 form a pair of right and left intermediate images having a parallax at the position of the photographic mask 43, and the ocular fundus images are observed using the monitor 41. When the ocular fundus is in focus, the pair of ocular fundus images formed at the position of the photographic mask 43 is overlapped and displayed as one ocular fundus image on the monitor 41. On the other hand, the pair of ocular fundus images is displayed as a double image in cases in which the ocular fundus is out of focus. Accordingly, in this case, the focusing lens 32 is adjusted and focusing is again performed so as to remove the double image.

A region 43b of the photographic mask 43 is a region in which only infrared light is transmitted, and the rectangular opening part 43a allows all of the bands of the light beam to be transmitted. A rectangular outline 43c corresponding to the rectangular opening part 43a is therefore displayed on the image taken by the imaging element 40 and displayed on the monitor 41, as illustrated by A in the upper right part of FIG. 1, and the examiner can confirm the size of the photographic range during stereoscopic photography.

The pair of right and left ocular fundus images with a parallax photographed at the position of the photographic mask 43 passes through the relay lens 47 and the two-aperture stop 50, and is made incident on the optical path splitting lenses 51, 52.

The relay lens 47 is disposed so as to form the exit pupil image of the first image-forming lens 33 on the optical path splitting lenses 51, 52. Specifically, with regards to the relay lens 47, the optical path splitting lenses 51, 52 are disposed in a position substantially conjugate with the anterior ocular segment 1b of the eye to be examined. The image of one aperture 31a of the two-aperture stop 31 is formed in proximity to the optical path splitting lens 52, and the image of the other aperture 31b is formed in proximity to the optical path splitting lens 51. Accordingly, there is an image-forming relationship (conjugate relationship) between each of the centers 31c, 31d of the apertures 31a, 31b of the two-aperture stop and the lens centers 52a, 51a of the optical path splitting lenses 52, 51.

Light rays 51b, 52b passing through the centers 51a, 52a of the optical path splitting lenses 51, 52 via the center of the photographic mask 43 reach points 51c and 52c of the imaging plane 53a. The distance between the reached points 51c, 52c is set to a length equal to substantially half the distance of the entire length L of the imaging plane 53a along the direction (vertical direction in FIG. 2) orthogonal to the photographic optical axis 48. Therefore, the ocular fundus image of the pair of right and left ocular fundus images formed by the optical path splitting lens 51 is formed separately on the upper half of the imaging plane 53a, and the ocular fundus image thereof formed by the optical path splitting lens 52 is formed separately on the lower half of the imaging plane 53a without a mutual overlap, making it possible to obtain ocular fundus images for three-dimensional viewing that efficiently uses the entire imaging plane 53a.

The path of the light ray drawn in thin dots in FIG. 2 shows that the left image having a parallax (lower part of FIG. 2) is formed on the left side (lower part) of the imaging plane, and the right image is formed on the right side (upper part). This allows the images having a parallax to be obtained with the relationship between the right and left matched without requiring a prism for transposing the right and left parts in the conventional manner.

The pair of right and left ocular fundus images having a parallax separated by the optical path splitting lenses 51, 52 can be observed in the eyepiece 62 via the mirror 61 when the visible-blocking/infrared-transmitting filter 13 is withdrawn from the optical path and the return mirror 60 is inserted into the optical path, as shown in FIG. 1. At this time, the observed ocular fundus images are a separated pair of right and left ocular fundus images 1c, 1d having a parallax, as shown by B in the upper right part of FIG. 1, and the examiner can view the ocular fundus in three dimensions.

The shutter switch 46 is operated in cases in which imaging is performed by the imaging element 53. The return mirror 60 is withdrawn from the optical path, and the strobe 14 is made to emit light in synchronization with this operation. The separated pair of right and left ocular fundus images 1c, 1d having a parallax is imaged on the imaging element 53 by the emission of light from the strobe 14 without overlap such as that seen in B in FIG. 1. The pair of ocular fundus images thus obtained is stored in the memory 54, and can be recalled at a later date for three-dimensional viewing by a three-dimensional viewing apparatus.

As shown in FIG. 1, a switch can be made from the pair of optical path splitting lenses 51, 52 to another pair of optical path splitting lenses 51', 52' having different magnifications. In this case, a pair of reduced or enlarged ocular fundus images having a parallax is photographed. At this time, a switch is made from the photographic mask 43 to the photographic mask 43' having a reduced or enlarged opening window in accordance with the magnification in conjunction with the switch.

The two-aperture stop 50 disposed in proximity to the optical path splitting lenses 51, 52 is not always necessary because the lens barrel of each of the lenses 51, 52 can be used.

Figure 5:
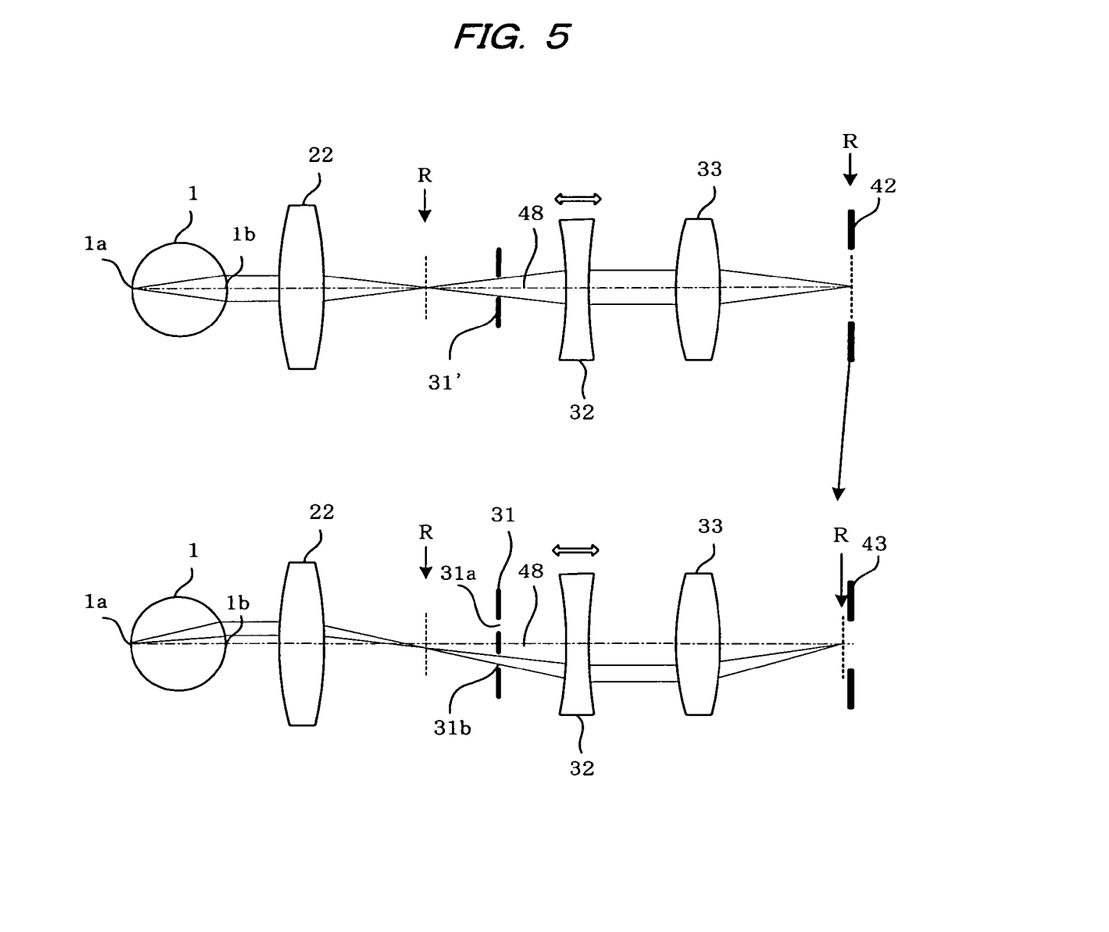
FIG. 5 is an illustrative view showing a state in which the focus is degraded during stereoscopic photography.

In monocular photography, the single-aperture stop 31' and the photographic mask 42 are inserted into the optical path as shown in the upper part of FIG. 5. The focusing lens 32 is moved to adjust the focus so as to obtain a clear ocular fundus image on the photographic mask 42 disposed in a position conjugate with the imaging planes of the CCD 40 and the CCD 53. Operating the shutter switch 46 in this state allows a focused, clear ocular fundus image to be photographed by the CCD 53.

However, when a switch is made to the two-aperture stop 31 and the photographic mask 43 to perform stereoscopic photography in this state, the apertures 31a, 31b of the two-aperture stop 31 are off-center from the photographic optical axis 48 as shown in the lower part of FIG. 5. Therefore, the ocular fundus cannot be clearly photographed because the plane R conjugate with the ocular fundus deviates from the photographic mask 43 and the imaging plane of the CCD 53.

Figure 6A:
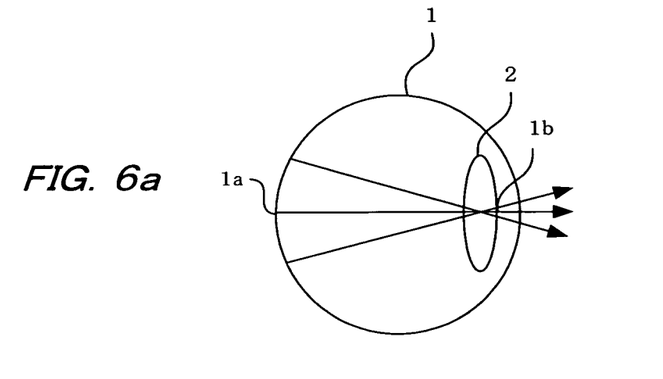
FIG. 6a is an illustrative view showing chromatic aberration inside an eye during monocular photography.
Figure 6B:
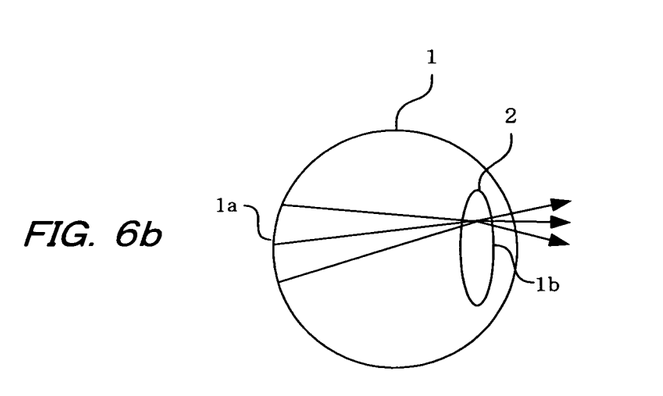
FIG. 6b is an illustrative view showing chromatic aberration inside an eye during stereoscopic photography.
Figure 6C:
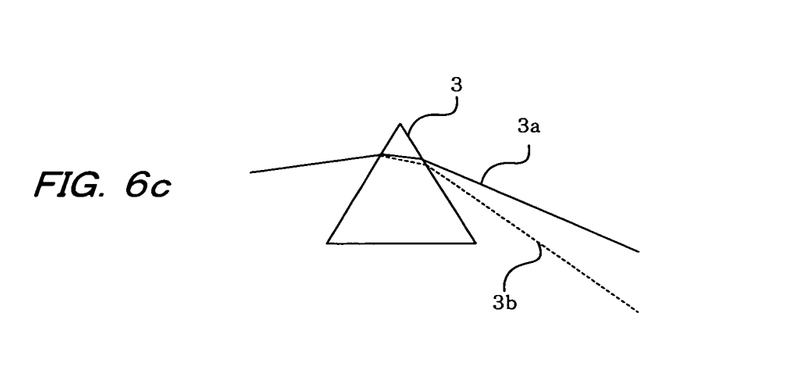
FIG. 6c is an illustrative view showing prism action inside an eye.

During monocular photography, chromatic aberration produced by the crystal lens 2 of the eye 1 to be examined is principally minute as shown in FIG. 6a because the ocular fundus 1a of the eye to be examined is photographed from an optical path that passes through the center of the pupil 1b of the eye 1 to be examined. However, during stereoscopic photography, a prism effect acts on the crystal lens 2 because the ocular fundus 1a of the eye to be examined is photographed from an optical path offset from the center of the pupil 1b of the eye 1 to be examined, as shown in FIG. 6b. Chromatic aberration occurs due to prism action on the crystal lens 2 during stereoscopic photography because a prism 3 separates a light ray into colors extending from a light ray 3a containing red to a light ray 3b containing violet, as shown in FIG. 6c.

Figure 7:
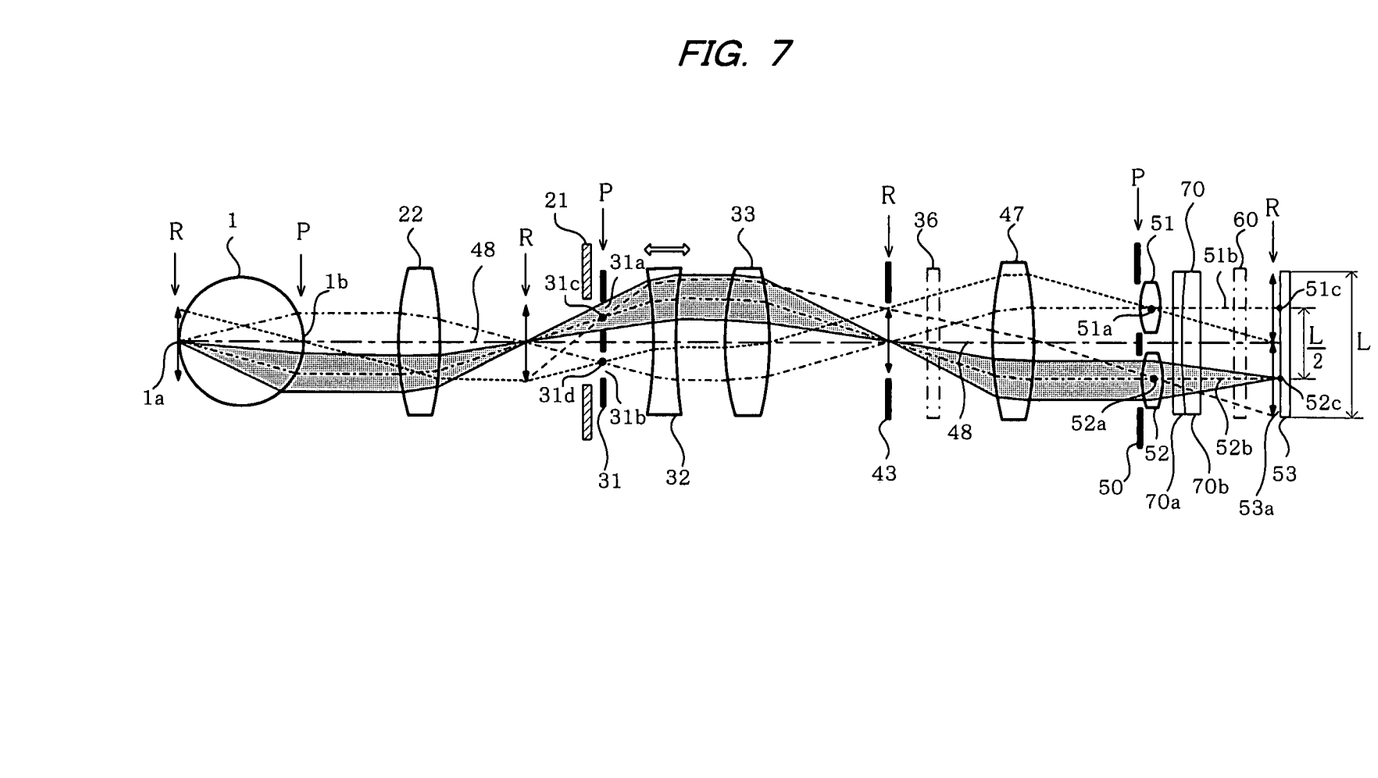
FIG. 7 is an optical diagram that corresponds to FIG. 2, where the optical path length and chromatic aberration during stereoscopic photography are corrected.
Figure 8:
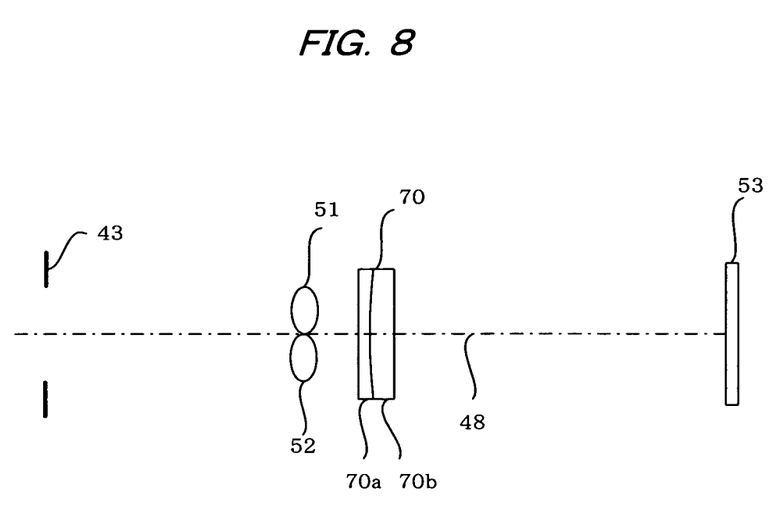
FIG. 8 is an optical diagram illustrating in a simplified manner an optical system for correcting optical path length and chromatic aberration.

In the present invention, a doublet lens 70 that serves as an optical element obtained by joining lenses 70a and 70b for correcting optical path length shift and chromatic aberration is inserted between the optical path splitting lenses 51, 52 and the CCD 53 when stereoscopic photography is performed, as shown in FIG. 7. This state is shown by the simplified optical diagram in FIG. 8 as well.

A sharply focused pair of ocular fundus images for three-dimensional viewing can be photographed by the CCD 53 even when a switch is made from monocular photography to stereoscopic photography because the doublet lens 70 corrects the optical path length and causes the plane R conjugate with the ocular fundus shown in FIG. 5 to move to the imaging plane of the CCD 40, 53 during stereoscopic photography. Ocular fundus images for three-dimensional viewing having an excellent image quality with minimal chromatic aberration can also be obtained because the composite lens 70 corrects chromatic aberration.

KEY TO THE SYMBOLS

1 Eye to be examined
21 Apertured total-reflection mirror
22 Objective lens
31 Two-aperture stop
31' Single-aperture stop
32 Focusing lens
33 Image-forming lens
40 Imaging element
42, 43 Photographic mask
46 Shutter switch
47 Relay lens
50 Two-aperture stop
51, 52 Optical path splitting lens
53 Imaging element
55 Image-forming lens for monocular photography
62 Eyepiece
70 Lens for correcting optical path length and chromatic aberration

The invention claimed is:

1. An ophthalmologic photography apparatus wherein an image of an ocular fundus of an eye to be examined is photographed by electronic imaging means, comprising:
a two-aperture stop disposed in a position conjugate with an anterior ocular segment of the eye to be examined for splitting a light beam reflected from the ocular fundus of the eye to be examined into a pair of right and left light beams having a parallax;
a first image-forming optical system that forms from the split light beams a pair of right and left optical fundus images as intermediate images; and
a second image-forming optical system that separates the pair of ocular fundus images formed as intermediate images into the right and left and re-forms them on an imaging plane of the electronic imaging means, the second image-forming optical system comprising a pair of optical path splitting lenses disposed in a position substantially conjugate with the two-aperture stop to split an optical path from the pair of ocular fundus images formed as intermediate images and separately re-forms the pair of ocular fundus images on the imaging plane of the electronic imaging means.

2. An ophthalmologic photography apparatus according to claim 1, wherein a lens for forming an exit pupil image in the first image-forming optical system on the second image-forming optical system is disposed between the pair of optical path splitting lenses and the plane on which the intermediate images are formed.

3. An ophthalmologic photography apparatus according to claim 1, wherein the distance between two points on the imaging plane reached by the light beams that pass through the lens centers of the pair of optical path splitting lenses via the centers of the intermediate images is equal to substantially half of the entire length of the imaging plane along a direction orthogonal to the photographic optical axis.

4. An ophthalmologic photography apparatus according to claim 1, wherein a second two-aperture stop is disposed at the position of each of the object-side openings of the pair of optical path splitting lenses in alignment with each of the openings.

5. An ophthalmologic photography apparatus according to claim 1, wherein the first image-forming optical system has a lens that is moved in the optical axis direction in accordance with the diopter of the eye to be examined to form sharply focused intermediate images.

6. An ophthalmologic photography apparatus according to claim 1, wherein a return mirror is provided between the second image-forming optical system and the electronic imaging means, and the ocular fundus images are guided to binocular viewing means when the return mirror is inserted into the optical path, the ocular fundus images being guided to the electronic imaging means when the return mirror is withdrawn from the optical path.

7. An ophthalmologic photography apparatus according to claim 1, wherein an optical path splitting means is provided between the position at which the intermediate images are formed and the second image-forming optical system, and a moving-image photography means for viewing is provided along the optical path split by the splitting means, the magnification of the image formed on the moving-image photography means being less than the magnification of the image formed by the second image-forming optical system.

8. An ophthalmologic photography apparatus according claim 1, wherein a photographic mask for determining a photographic range for the ocular fundus is disposed on a plane on which the intermediate images are formed.

9. An ophthalmologic photography apparatus according to claim 8, wherein a switch is made from the pair of optical path splitting lenses to another pair of optical path splitting lenses having different magnifications, and an opening of the photographic mask is changed in shape in conjunction with the switch in magnification.

10. An ophthalmologic photography apparatus according to claim 1, wherein a switch is made from the two-aperture stop to a single-aperture stop, and in conjunction therewith a switch is made from the pair of optical path splitting lenses to a single image-forming lens to enable stereoscopic photography and monocular photography.

11. An ophthalmologic photography apparatus according to claim 10, wherein an optical element for correcting optical path length and chromatic aberration is inserted between the pair of optical path splitting lenses and the electronic imaging means when a switch is made from monocular photography to stereoscopic photography.

* * * * *